United States Patent [19]
Johnson et al.

[11] 4,335,249
[45] Jun. 15, 1982

[54] HERBICIDAL DIPHENYL ETHERS, SULFIDES, SULFOXIDES AND SULFONES

[75] Inventors: Wayne O. Johnson, Warminster; Roy Y. Yih, Doylestown, both of Pa.

[73] Assignee: Rohm and Haas Company, Philadelphia, Pa.

[21] Appl. No.: 710,074

[22] Filed: Jul. 30, 1976

Related U.S. Application Data

[63] Continuation-in-part of Ser. No. 610,481, Sep. 3, 1975, abandoned.

[51] Int. Cl.³ .............................................. C07C 69/76
[52] U.S. Cl. ........................................ 560/11; 560/8; 260/465 D; 260/465 F; 562/426; 562/429; 564/162; 71/98; 71/103; 71/108; 71/109
[58] Field of Search ................... 71/108, 109, 98, 103; 260/473 G, 465 D, 465 F; 560/61, 11, 18; 80/11, 8; 562/426, 429; 564/162

[56] References Cited

U.S. PATENT DOCUMENTS

| | | | |
|---|---|---|---|
| 3,322,525 | 5/1967 | Martin et al. | 71/2.3 |
| 3,928,416 | 12/1975 | Bayer | 560/62 |
| 3,954,422 | 5/1976 | Becker et al. | 71/108 |
| 3,957,852 | 5/1976 | Fujikawa et al. | 260/476 |

FOREIGN PATENT DOCUMENTS

| | | | |
|---|---|---|---|
| 831469 | 11/1975 | Belgium | 560/62 |
| 121015 | 7/1976 | German Democratic Rep. | 560/62 |
| 14782 | 5/1976 | Iran | 560/62 |

*Primary Examiner*—Paul J. Killos
*Attorney, Agent, or Firm*—George W. F. Simmons; William E. Lambert, III; Terence P. Strobaugh

[57] ABSTRACT

Diphenyl ethers of the formula

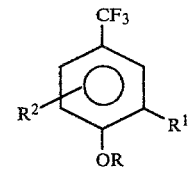

wherein
$R^1$ is hydrogen or halogen,
$R^2$ is hydrogen, halogen, or cyano,
R is

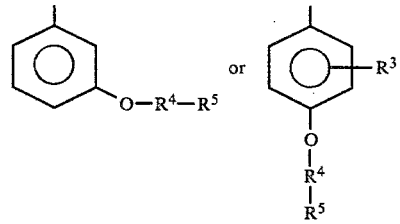

wherein
$R^3$ is hydrogen, halogen, nitro, alkyl, or alkoxy,
$R^4$ is a divalent alkylene radical, and
$R^5$ is cyano or —$COR^6$, wherein $R^6$ is alkoxy, hydroxy or salt thereof, allyloxy, alkoxyalkoxy, amino, alkyl or dialkyl amino, aminoalkoxy, or alkyl or dialkylaminoalkoxy, and diphenyl sulfides, sulfoxides, and sulfones of the formula

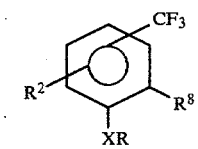

wherein
$R^8$ is hydrogen, halogen, cyano, nitro, alkyl, alkoxy, or trifluoromethyl,
$R^2$ is hydrogen, halogen or cyano,
X is sulfur, sulfinyl, or sulfonyl, and
R is as defined above, and compositions containing these compounds exhibit herbicidal activity.

19 Claims, No Drawings

HERBICIDAL DIPHENYL ETHERS, SULFIDES, SULFOXIDES AND SULFONES

CROSS REFERENCE TO RELATED APPLICATION

This application is a continuation-in-part of copending application Ser. No. 610,481, filed Sept. 3, 1975, abandoned.

This invention relates to novel compounds which show activity as herbicides, to novel herbicidal compositions which contain these compounds, and to new methods of controlling weeds with these herbicidal compositions.

Certain diphenyl ethers have been shown to be effective weed control agents. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition. Furthermore, the diphenyl ethers heretofore disclosed as herbicides are not completely effective. An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise be dissipated so as not to poison the soil permanently. The known diphenyl ether herbicides fall short of these ideals, and it would thus be desirable to have new herbicides which show even more selective control of undersirable plants among desirable crop plants or which complement the known diphenyl ethers in activity.

In accordance with the present invention, there is provided a new class of novel diphenyl ethers having the formula

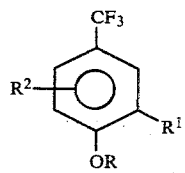

(I)

wherein
- $R^1$ is a hydrogen atom, or a halogen atom, preferably a fluorine atom or a chlorine atom,
- $R^2$ is a hydrogen atom, a halogen atom, or a cyano group,
- R is a group of the formula

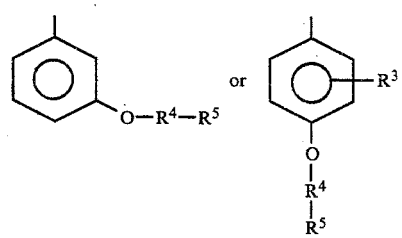

wherein
- $R^3$ is a hydrogen atom, a halogen atom, preferably a fluorine atom or a chlorine atom, a nitro group, an alkyl group, preferably having 1 to 4 carbon atoms, or an alkoxy group, preferably having 1 to 4 carbon atoms,
- $R^4$ is a divalent alkylene group, preferably having 1 to 5 carbon atoms, and
- $R^5$ is a cyano group, or a group of the formula $-COR^6$, wherein
- $R^6$ is an alkoxy group, preferably having 1 to 10 carbon atoms, a hydroxy group, or an agronomically-acceptable salt thereof, an allyloxy group, an alkoxyalkoxy group, preferably having 1 to 4 carbon atoms in each alkoxy moiety, an amino group, an alkoxy or dialkylamino group, preferably with alkyl substituents having 1 to 4 carbon atoms, an aminoalkoxy group, preferably having 1 to 4 carbon atoms, or an alkyl- or dialkylaminoalkoxy group, preferably having 1 to 4 carbon atoms in the alkoxy moiety and in each alkyl substituent, and a new class of diphenyl sulfides, sulfoxides, and sulfones having the formula

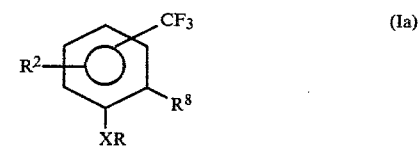

(Ia)

wherein
- $R^8$ is hydrogen atom, a halogen atom, preferably a fluorine atom or a chlorine atom, a cyano group, a nitro group, an alkyl group, preferably having 1 to 4 carbon atoms, an alkoxy group, preferably having 1 to 4 carbon atoms, or a trifluoromethyl group,
- X is a sulfur atom, a sulfinyl group ($-SO-$), or a sulfonyl group ($-SO_2-$), and
- R and $R^2$ are as defined above.

The alkyl portion of the alkyl-containing $R^3$, $R^6$, $R^7$, and $R^8$ substituents as well as the alkylene group of $R^4$ can have either a straight- or branched-chain spatial configuration. These novel compounds have been found to show unexpected activity as selective weed control agents.

In the diphenyl ethers of the invention, it is preferred that $R^2$ and $R^3$ are hydrogen atoms, when $R^5$ is a cyano group, $R^4$ is a group of the formula $-CHR^7-$, wherein $R^7$ is a hydrogen atom or a ($C_1$-$C_4$)alkyl group, preferably a methyl group, and that when $R^5$ is a group of the formula $-COR^6$, $R^4$ is a group of the formula $-CHR^7CH_2(CH_2)_n-$, wherein $R^7$ is as defined above and is preferably a methyl group, and n is 0 or 1.

Typical salts embraced by Formulas I and Ia, salts of those compounds in which $R^6$ is a hydroxy group, include alkali metal salts, such as sodium and potassium salts, alkaline earth metal salts, such as calcium and barium salts, heavy metal salts, such as copper and zinc salts, amine salts, such as ammonium, ethanolammonium, diethanolammonium, triethanolammonium, triethylammonium, dimethylammonium, diisopropylammonium, t-butylammonium, t-octylammonium, and similar agronomically-acceptable salts.

Examples of the compounds of the invention embraced by Formulas I and Ia include:

Ethyl 2-[4-(2-chloro-4-trifluoromethylphenoxy)-phenoxy] propionate
Methyl 2-[4-(2-chloro-4-trifluoromethylphenoxy)-phenoxy] butyrate
Propyl 2-[4-(2-chloro-4-trifluoromethylphenoxy)-phenoxy] acetate
Methyl 2-[4-(2-chloro-4-trifluoromethylphenoxy)-phenoxy] propionate
Ethyl 2-[3-(2-chloro-4-trifluoromethylphenoxy)-phenoxy] propionate
Methyl 2-[2-(2-chloro-4-trifluoromethylphenoxy)-phenoxy] butyrate
Ethyl 2-[4-(2-chloro-4-trifluoromethylphenoxy)-2-methoxyphenoxy] propionate
Isopropyl 2-[4-(2-chloro-4-trifluoromethylphenoxy)-2-nitrophenoxy] butyrate
Methyl 2-[4-(2-chloro-4-trifluoromethylphenoxy)-2-ethoxyphenoxy] propionate
Sodium 2-[4-(2-chloro-4-trifluoromethylphenoxy)-phenoxy] propionate
Methyl 2-[4-(2,6-dichloro-4-trifluoromethylphenoxy)-2-ethoxyphenoxy] propionate
Ethyl 2-[4-(2-chloro-6-fluoro-4-trifluoromethylphenoxy)phenoxy] propionate
Methyl 2-[4-(4-trifluoromethylphenoxy)phenoxy] crotonate
2-[4-(2-chloro-4-trifluoromethylphenoxy)phenoxy] propionic acid
2-[4-(2-chloro-4-trifluoromethylphenoxy)-2-methoxyphenoxy] butyric acid
N,N-Diethyl 2-[4-(2-chloro-4-trifluoromethylphenoxy)-phenoxy] propionamide
Ethyl 2-[4-(2-chloro-4-trifluoromethylphenylthio)-phenoxy] propionate
Methyl 2-[4-(2-chloro-4-trifluoromethylphenoxy)-2-chlorophenoxy] propionate
2-[4-(2-chloro-4-trifluoromethylphenoxy)phenoxy] propionitrile
2-[4-(2-chloro-4-trifluoromethylphenoxy)-2-methylphenoxy] acetonitrile
2-[4-(2-chloro-4-trifluoromethylphenoxy)-2-chlorophenoxy] propionitrile
2-[4-(2-Chloro-4-trifluoromethylphenoxy)-2-methoxyphenoxy] butyronitrile
N,N-Dimethyl 2-[4-(2-chloro-4-trifluoromethylphenoxy)-2-methylphenoxy] butyramide
N,N-Di-sec-butyl 2-[4-(2-chloro-4-trifluoromethylphenoxy)2-chlorophenoxy] acetamide
N-Butyl-N-Methyl 2-[4-(2,6-dichloro-4-trifluoromethylphenoxy)phenoxy] propionamide
Ethyl 2-[4-(2-chloro-4-trifluoromethylphenylsulfinyl)-phenoxy] butyramide
Methyl 2-[4-(2-chloro-4-trifluoromethylphenylsulfonyl)-2-methylphenoxy] crotonamide
Ethyl 2-[4-(3-trifluoromethylphenylthio)phenoxy] propionate,
N,N-Dimethylaminoethyl 2-[3-(2-cyano-4-trifluoromethylphenylthio)phenoxy] valeramide
2-[4-(3-Trifluoromethylphenylsulfinyl)phenoxy] propionic acid
Triethanolammonium 2-[4-(2-trifluoromethylphenylsulfonyl)phenoxy] propionate
Ethyl 3-[4-(2-methoxy-4-trifluoromethylphenylthio)-phenoxy] propionate
2-[4-(2-Nitro-4-trifluoromethylphenylsulfinyl)phenoxy] propionitrile
Isobutyl 2-[4-(2-ethyl-4-trifluoromethylphenylsulfonyl)phenoxy] butyrate
Ethyl 2-[4-(3-chloro-4-trifluoromethylphenoxy)-phenoxy] propionate
Ammonium 2-[4-(2,5-dichloro-4-trifluoromethylphenoxy)phenoxy] propionate
2-[2-Methoxy-4-(2-chloro-4-trifluoromethylthio)-phenoxy] butyronitrile
2-[4-(2-Cyano-4-trifluoromethylphenoxy)phenoxy] propionic acid The novel compounds of the invention are useful both as selective preemergence and preferably, as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the plants have emerged and during their growth period. The compounds of the invention are most effective against monocot weed species, and can be advantageously employed to control monocot weeds in such crops as soybeans, peanuts, cotton, wheat, barley, rice, and the like.

The compounds of the invention can be applied in any amount which will give the required control of weeds. A preferred rate of application of the herbicides of the invention is from about 1/16 to about 8 pounds of the active compound per acre, and most preferably about ¼ to about 2 pounds of the active compound per acre.

Under some conditions, the compounds of the invention may be advantageously incorporated into the soil or other growth medium prior to planting a crop. This preplant incorporation can be carried out by any convenient means, including by simple mixing with the soil, by applying the herbicide to the surface of the soil and then disking or dragging into the soil to the desired depth, or by employing a liquid carrier to accomplish the necessary penetration and impregnation.

The compounds of the invention can be applied to the growth medium or to plants to be treated either alone or, as is generally done, as components in herbicidal compositions or formulations which also comprise an agronomically-acceptable carrier. By agronomically-acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in post-emergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the active compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain-hulls, or similar material. A solution of one or more of the active compounds in a volatile organic solvent can be sprayed or mixed with the granular solid and the solvent then removed by evaporation. The granular material can have any suitable size, with a preferable size range of 16 to 60 mesh. The active compound will usually comprise about 2 to 15% of the granular formulation.

The compounds of the invention can also be mixed with fertilizers or fertilizing materials before their application. In one type of solid fertilizing composition in which the compounds of the invention can be used, particles of a fertilizer or fertilizing ingredients, such as ammonium sulfate, ammonium nitrate, or ammonium phosphate, can be coated with one or more of the ethers. The solid compounds and solid fertilizing material can also be admixed in mixing or blending equipment, or they can be incorporated with fertilizers in granular formulations. Any relative proportion of herbicide and fertilizer can be used which is suitable for the crops and weeds to be treated. The active compound will commonly be from about 5% to about 25% of the fertilizing composition. These compositions provide fertilizing materials which promote the rapid growth of desired plants, and at the same time control the growth of undesired plants.

The compounds of the invention can be applied as herbicidal sprays by methods commonly employed, such as convention high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with compounds of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
2-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts Carbamic Acid Derivatives ethyl N,N-di(n-propyl)thiolcarbamate
propyl N,N-di(n-propyl)thiolcarbamate ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
S-ethyl hexahydro-1H-azepine-1-carbothioate
S-4-chlorobenzyl N,N-diethylthiocarbamate
isopropyl N-phenylcarbamate
isopropyl N-(m-chlorophenyl)carbamate
4-chloro-2-butyl N-(m-chlorophenyl)carbamate
methyl N-(3,4-dichlorophenyl)carbamate
methyl sulfanilylcarbamate

Phenols dinitro-o-(sec-butyl)phenol and its salts
pentachlorophenol and its salts

Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1,-diethylurea
1-(2-methylcyclohexyl)-3-phenylurea
1-(5-t-butyl-1,3,4-thiadiazol-2-yl)-1,3-dimethylurea
3-(3-chloro-4-methylphenyl)-1,1-dimethylurea
3-(3-chloro-4-methoxyphenyl)-1,1-dimethylurea
dichloral urea

Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine
2-(4-chloro-6-ethylamino-s-triazine-2-yl)amino-2-methylpropionitrile
4-amino-6-t-butyl-3-methylthio-1,2,4-triazine-5(4H)-one
3-cyclohexyl-6-dimethylamino-1-methyl-s-triazine-2,4-(1H,3H)-dione

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether
2-chloro-4-trifluoromethyl-4'-nitrodiphenyl ether
2-chloro-4-trifluoromethyl-3'-ethoxy-4'-nitrodiphenyl ether
2-chloro-4-trifluoromethyl-3'-carbethoxy-4'-nitrodiphenyl ether
2-chloro-4-trifluoromethyl-3'-(1-carbethoxy)ethoxy-4'-nitrodiphenyl ether

Anilides

N-(3,4-dichlorophenyl)propionamide
N-(3,4-dichlorophenyl)methacrylamide
N-(3-chloro-4-methylphenyl-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
diphenylacetonitrile
3,5-dibromo-4-hydroxybenxonitrile
3,5-diiodo-4-hydroxybenzonitrile

Other Organic Herbicides 2-chloro-N,N-diallylacetamide
N-(1,1-dimethyl-2-propnyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazine-(4)3H-one-2,2-dioxide
6,7-dihydrodipyridol[1,2-a:2';1'-c]pyrazidinium salts
1,1'-dimethyl-4,4'-bipyridinium salts
3,4,5,6-tetrahydro-3,5-dimethyl-2-thio-2H-1,3,5-thiadiazine
1,2-dimethyl-3,5-diphenylpyrazolium methyl sulfate
N-sec-butyl-2,6-dinitro-3,4-xylidine
N-sec-butyl-4-t-butyl-2,6-dinitroaniline
$N^3,N^3$-diethyl-2,4-dinitro-6-trifluoromethyl-1,3-phenylenediamine
1,1,1-trifluoro-(4'-phenylsulfonyl)methanesulfono-o-toluidine
2-(1-naphthoxy)-N,N-diethylpropionamide
2-t-butyl-4-(2,4-dichloro-5-isopropoxyphenyl)-1,3,4-oxadiazolin-5-one
4-chloro-5-methylamino-2-(α,α,α-trifluoro-m-tolyl)3(2H)pyridazinone
N-cyclopropylmethyl-α,α,α-trifluoro-2,6-dinitro-N-propyl-p-toluidine
N-phosphonomethylglycine When mixtures of herbicides are employed, the relative proportions which are used will depend upon the crop to be treated and the degree of selectivity in weed control which is desired.

The compounds of the invention or their precursors are prepared by several different reaction routes. In one typical synthetic method a halobenzene of the formula

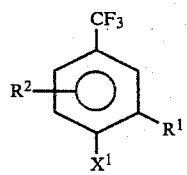 (II)

wherein $R^1$ and $R^2$ are as defined above and $X^1$ is a halogen atom, is reacted with a phenol of the formula

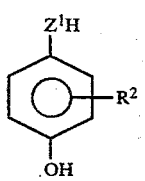 (III)

wherein $R^3$ is as defined above and $Z^1$ is an oxygen atom or a sulfur atom, to form a compound of the formula

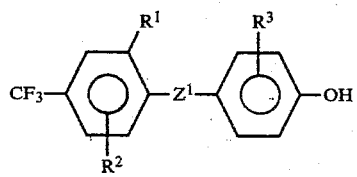 (IV)

wherein $R^1$, $R^2$, $R^3$, and $Z^1$ are as defined above. This reaction is generally carried out at a temperature of about 25° to about 150° C., in the presence of a base such as potassium hydroxide, sodium hydroxide, potassium carbonate, sodium carbonate, or the like, with an aprotic polar solvent, such as dimethylsulfoxide, dimethylformamide, sulfolane, hexamethylphosphoric triamide, 1-methyl-2-pyrrolidinone, and the like. The phenol of Formula IV is then reacted with a compound of the formula

Y-$R^4$-$R^5$ (V)

wherein Y is a chlorine or a bromine atom, and $R^4$ and $R^5$ are as defined above. This reaction is generally carried out at a temperature of about 25° to about 140° C., in the presence of a base, such as potassium hydroxide, sodium hydroxide, potassium carbonate, sodium carbonate, or the like with an aprotic polar solvent, such as dimethylsulfoxide, dimethylformamide, dioxane, a ketone, such as acetone, methyl ethyl ketone, or the like, acetonitrile ethylene glycol dimethyl ether, tetrahydrofuran, and the like.

The phenol of Formula IV can also be prepared by reacting a compound of Formula I with a compound of the formula

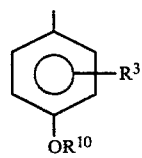 (VI)

wherein $R^3$ is defined above and $R^{10}$ is an allyl group or a benzyl group, this reaction is carried out under the same conditions as the reaction of compounds II and III. The resultant diphenyl ether is then hydrogenated using palladium on charcoal, platinum oxide, or the like as a catalyst, in an alcohol, such as methanol or ethanol, ethyl acetate, acetic acid, or the like as a solvent, at ambient temperatures, or at a temperature of about 0° to about 120° C., to yield the phenol.

Compounds of the invention in which $R^3$ is a halogen atom, a nitro group, or a ($C_1$-$C_4$)alkyl group can also be prepared by reacting a compound of Formula II with a compound of the formula

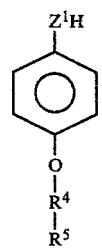 (VII)

to give a compound of the formula

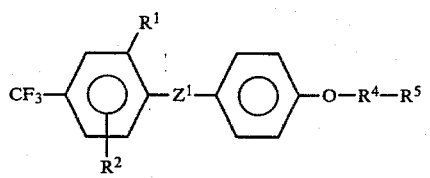 (VIII)

using the same general conditions as the reaction of compounds II and III. The desired compound can then be obtained by direct electrophilic halogenation, nitration, or alkylation of the compound of Formula VIII. Typical halogenations can be carried out by reaction with an excess or equimolar amount of a halogenating agent, such as chlorine, in the presence of a transition metal chloride, such as ferric chloride, as a catalyst, in an inert solvent such as chlorobenzene, ethylene dichloride, or other chlorinated hydrocarbon, at a temperature of about 25° to about 120° C. Typical nitrations can be carried out with an excess or equimolar amount of a nitrating agent, such as nitric acid, in sulfuric acid or acetic anhydride/sulfuric acid, optionally with an appropriate inert solvent, at a temperature of about 25° to about 120° C. Typical alkylations can be carried out by reaction with an excess or equimolar amount of an appropriate alkylating agent, such as a lower alkyl chloride, bromide, or iodide, in the presence of a Lewis acid, such as ferric chloride, titanium chloride, aluminum trichloride, stannic chloride, or the like, as a catalyst, in an inert solvent, such as carbon disulfide, ethylene dichloride, perchloroethylene, or the like, at a temperature of about 25 to about 120° C.

The compounds of the invention in which $R^5$ is a carboxy group can be prepared by hydrolyzing a compound of the invention in which $R^5$ is a cyano group, a carbamoyl group, or a carbalkoxy group. The hydrolysis can be either acid catalyzed, using sulfuric acid, anhydrous hydrochloric acid in methanol, acetic acid/boron trifluoride, or similar acid catalyst, or base catalyzed using potassium hydroxide in methanol, barium hydroxide in methanol, or similar base catalyst, optionally with an appropriate inert solvent, at a temperature of about 20° to about 130° C. Suitable reaction conditions for carrying out the desired hydrolysis can be varied, depending on the group to be hydrolyzed and the various substituents on the diphenyl ether or diphenyl sulfide nucleus, and such modifications will be apparent to those skilled in the art.

The diphenyl sulfides of the invention can also be prepared by reacting a phenol of Formula III in which $Z^1$ is a sulfur atom with cuprous oxide to produce the cuprous salt of the thiophenol. This reaction can be carried out, for example, in refluxing ethanol. The cuprous salt is generally not isolated, but reacted directly with a halobenzene of Formula II in which $X^1$ is a bromine atom, in a solvent such as quinoline, dimethylformamide or the like, in the presence of a nitrogen base such as pyridine, or the like, at a temperature of about 50° to about 100° C. The resulting phenol is then further reacted as noted above to produce the desired diphenyl sulfide. Other suitable methods for preparing the diphenyl sulfides of the invention include displacement of aromatic diazonium salts with a salt, such as a sodium salt, of a thiophenol of Formula III. Diphenyl sulfides, sulfoxides, and sulfones of the invention can also be prepared by the reaction of an appropriate aromatic sulfenyl, sulfinyl, or sulfonyl halide with a substituted phenol or anisole.

The compounds of the invention in which Z is a sulfinyl group can be prepared by oxidizing the corresponding diphenyl sulfide of Formula IV or VIII using an oxidizing agent such as an excess or equimolar amount of sodium periodate in methanol/water, at about 0° to about 60° C., or one equivalent of hydrogen peroxide in acetic acid, at about 0° to about 50° C., optionally using an acidic catalyst, such as sulfuric acid. The compounds of the invention in which Z is a sulfonyl group can be prepared by oxidizing the corresponding diphenyl sulfide, for example, with at least two equivalents of hydrogen peroxide in acetic acid, at about 0° to about 120° C., optionally using an acidic catalyst such as sulfuric acid. Other methods which are apparent to those skilled in the art for preparing the compounds of the invention or their precursors can also be used.

The following examples will further illustrate this invention but are not intended to limit it in any way. In Table I, typical diphenyl ethers of the invention are listed with their melting or boiling points and elemental analyses. In Table II, typical diphenyl sulfides, sulfones, and sulfoxides are listed with their melting or boiling points and elemental analyses. Specific, illustrative preparations of the compounds of Examples 1 to 6, 40, 41, 48 and 49 are also set forth. All temperatures are in degrees centigrade and parts and percentages by weight, unless otherwise indicated.

EXAMPLE 1

Preparation of Ethyl 2-[4-(2-chloro-4-trifluoromethylphenoxy)phenoxy]propionate

Preparation A

A. 4-Benzyloxyphenyl 2-chloro-4-trifluoromethylphenyl ether

To as flask equipped with a stirrer, thermometer, condenser and drying tube are charged 3,4-dichlorobenzotrifluoride (43 g., 0.20 mole), potassium 4-benzyloxyphenate (47.5 g., 0.20 mole-prepared from hydroquinone monobenzylether using potassium hydroxide pellets dissolved in methanol and removal of the solvent in vacuo and subsequent precipitation in ether) and dimethyl sulfoxide (400 ml.). The reaction mixture is then warmed to 120° C. and maintained at 135° C. for 3 hours, cooled, poured into water (3 liters) and extracted into hexane (500 ml., then 300 ml., then 200 ml.) and the combined hexane extracts washed again with water (200 ml.), dried with anhydrous magnesium sulfate, and the solvent removed in vacuo to give 52.6 g. (70% yield) of 4-benzyloxyphenyl 2-chloro-4-trifluoromethylphenyl ether, mp 63°-6° C., which is recrystallized from methanol to give white crystals, mp 69°-71° C.

B. 4-(2-Chloro-4-trifluoromethylphenoxy)phenol

4-Benzyloxyphenyl 2-chloro-4-trifluoromethylphenyl ether (25 g., 0.066 mole), purified by recrystallization from methanol, ethyl acetate (200 ml.) and 10% palladium on charcoal (1.0 g.) are charged to a 2-liter Paar hydrogenation bottle and shaken in a hydrogen atmosphere (40-45 psi) until hydrogen uptake ceases. The catalyst is then removed by filtration and the solvent and toluene are removed in vacuo to give 17.9 g. (94% yield) of 4-(2-chloro-4-trifluoromethylphenoxy)phenol, mp 55°-6° C.

C. Ethyl 2-[4-(2-Chloro-4-trifluoromethylphenoxy)phenoxy]propionate 4-(2-Chloro-4-trifluoromethylphenoxy)phenol (8.66 g., 0.030 mole), anhydrous potassium carbonate (6.0 g., >0.030 mole) ethyl 2-bromopropinate (5.43 g., 0.030 mole), and dimethyl sulfoxide (50 ml.) are charged to a flask, (equipped with a condenser, stirrer, drying tube and thermometer) and the reaction mixture is stirred at room temperature for about 3 days. The reaction mixture is then poured into water (300 ml.) and the product is extracted into carbon tetrachloride, 150 ml., then 75 ml., the combined organic layer washed again with water (100 ml.), decanted, dried with anhydrous magnesium sulfate, and the solvent removed in vacuo to give 10.9 g. (93% yield) of ethyl 2-[4-(2-chloro-4-trifluoromethylphenoxy)phenoxy]propinate as a colorless oil. Anal. Calcd. for $C_{18}H_{16}ClF_3O_4$: C, 55.60; H, 4.14; Cl, 9.11; F, 14.65. Found: C, 55.79; H, 4.20, Cl, 9.48; F, 14.62.

Preparation B

A. 4-(2-Chloro-4-trifluoromethylphenoxy)phenol

The dipotassium salt of hydroquinone (403.7 g.—prepared by dissolving two molar equivalent of hydroquinone and four molar equivalents of potassium hydroxide pellets in methanol followed by removal of the alcohol in vacuo and trituration of the residue with tetrahydrofuran) is slurried in dimethyl sulfoxide (1.7 liters). This is further dried by adding toluene (300 ml.) and subsequent azeotropic distillation of water and methanol using a Dean-Stark trap over a 6-hour period. Then 3,4-dichlorobenzotrifluoride (322.5 g., 1.5 mole) is charged to the reaction vessel and the mixture heated at 130° C. for 8.5 hours and the reaction mixture cooled and worked up in portions. The reaction mixture (800 ml portion) is poured into water (3.5 liters) and adjusted to pH 11 with 50% aqueous sodium hydroxide. The basic reaction mixture is then extracted with toluene (300 ml) and the aqueous layer decanted and acidified to pH 1 (conc. HCl), the product extracted into methylene chloride (2×300 ml) and the combined methylene chloride extracts washed again with water (2×300 ml), dried with anhydrous sodium sulfate, and the solvent removed in vacuo to give 404 g. of the desired phenol.

The toluene extracts are combined and diluted with an equal volume of hexane and washed with water (3×1 liter), decanted, dried with anhydrous sodium sulfate and the solvent removed in vacuo to give 55.2 g of a yellow solid-1,4-(Bis-2-chloro-4-trifluoromethylphenoxy)benzene.

B. Ethyl 2-[4-(2-Chloro-4-trifluoromethylphenoxy)phenoxy]propionate 4-(2-Chloro-4-trifluoromethylphenoxy)phenol (243.5 g., 0.85 mole), ethylene glycol dimethyl ether (glyme, 2 liters), ethyl 2-bromopropionate (154 g., 0.85 mole) and anhydrous potassium carbonate (152 g., 1.1 mole) are charged to a flask and the mixture refluxed for 19 hours, cooled, the inorganics removed by filtration, the solvent removed in vacuo and the residue redissolved in toluene, dried with anhydrous sodium sulfate, and the toluene removed in vacuo to give 258 g of ethyl 2-[4-(2-chloro-4-trifluoromethylphenoxy)phenoxy] propionate. Anal. Calcd. for $C_{18}H_{16}ClF_3O_4$: C, 55.60; H, 4.14; Cl, 9.11; F, 14.65. Found: C, 55.68; H, 4.09; Cl, 9.35; F, 14.46.

EXAMPLE 2

Preparation of Ethyl 2-[3-(2-chloro-4-trifluoromethylphenyl)phenoxy]propionate

Preparation A 3-(2-Chloro-4-trifluoromethylphenoxy) phenol (14.4 g., 0.05 mole), dimethyl sulfoxide (100 ml.), anhydrous potassium carbonate (13.8 g., 0.10 mole, excess) and ethyl 2-bromopropionate (9.05 g., 0.05 mole) are charged to a flask equipped with a stirrer, condenser and drying tube and stirred at room temperature for five days. The reaction mixture is then poured into water (600 ml.) and the aqueous mixture extracted with carbon tetrachloride (2×200 ml.) and the combined carbon tetrachloride extracts are again washed with water (200 ml.), dried with anhydrous sodium sulfate, and reduced in vacuo (0.10 mm) to give the desired product (15.2 g., 78% yield). Nmr analysis confirms only O-alkylation and gas-liquid chromatographic analysis suggests the expected amount of CF$_3$-ring positional isomer. Anal. Calcd. for $C_{18}H_{16}ClF_3O_4$: C, 55.61; H, 4.14; Cl, 9.11; F, 14.66. Found: C, 55.27; H, 4.14; Cl, 9.40; F, 13.80.

Preparation B 3-(2-Chloro-4-trifluoromethylphenoxy)phenol (14.4 g., 0.05 mole), dimethyl sulfoxide (50 ml.), anhydrous potassium carbonate (15.0 g., slight excess) and ethyl 2-chloropropionate (7 g., slight excess) are charged to a flask equipped with a stirrer, condenser, drying tube and thermometer and the reaction mixture is warmed to 100°–105° C. After 2½ hours at 100°–105° C., gas-liquid chromatographic analysis of an aliquot (diluted with water and extracted into carbon tetrachloride) indicate the reaction is complete (product eluting at 245° C.).

EXAMPLE 3

Preparation of Ethyl 2-[4-(2-Chloro-4-trifluoromethylphenylthio)phenoxy]propionate To a stirred solution containing 12.6 g. (0.1 mole) of 4-mercaptophenol in 75 ml. of dimethylformamide is added 6.6 g. (0.1 mole) of 85% potassium hydroxide pellets in one portion at 25°. The resultant mixture is heated until all of the potassium hydroxide has dissolved, whereupon it is cooled to about 80° and 21.6 g. (0.1 mole) of 3,4-dichlorobenzotrifluoride is added over a period of 15 minutes. The addition is accompanied by an immediate precipitation of potassium chloride. The resultant slurry is heated at 100° to effect complete reaction, at which time it is cooled to 25°, diluted to a volume of 300 ml. with a dilute hydrochloric acid solution, and extracted three times with ether. The combined organic extracts are washed with a dilute hydrochloric acid solution, water, a saturated sodium chloride solution, dried with anhydrous magnesium sulfate, and concentrated in vacuo. Purification of the crude white solid is effected by recrystallization from hexane-ether to afford 17.1 g. of 4-(2-chloro-4-trifluoromethylphenylthio)phenol, MP 118°–120°.

A mixture containing 6.09 g. (0.02 mole) of 4-(2-chloro-4-trifluoromethylphenylthio)phenol, 3.04 g. (0.22 mole) of potassium carbonate, 3.62 g. (0.02 mole) of ethyl 2-bromopropionate, and 100 ml. of dimethyl sulfoxide is stirred at 25° for sufficient time to affect complete reaction, as indicated by vapor-phase chromatographic techniques. Upon dilution with 500 ml. of water and 100 ml. of a 3.0 molar hydrochloric acid solution the product is extracted with ether. The combined organic extracts are washed with a 5% potassium carbonate solution, water, a saturated sodium chloride solution, dried with anhydrous magnesium sulfate, and concentrated in vacuo. Removal of the last traces of solvent is accomplished by subjecting the yellow liquid to high vacuum (0.05 mm) at 70° to afford 7.95 g. of ethyl 2-[4-(2-chloro-4-trifluoromethylphenylthio)phenoxy] propionate. Recrystallization from methanol affords white crystals, mp. 64.5°–66.5°.

EXAMPLE 4

Preparation of Methyl 2-[4-(2-chloro-4-trifluoromethylphenoxy)phenoxy]propionate 4-(2-Chloro-4-trifluoromethylphenoxy)phenol (4.0 g., 0.014 mole), methyl 2-bromopropionate (2.35 g., 0.014 mole), anhydrous potassium carbonate (2.8 g., 0.20 mole) and glyme (50 ml) are charged to a flask and heated at reflux for 18 hours, the reaction mixture cooled, the inorganics removed by filtration and the solvent removed in vacuo to give 5.0 g., of product. Anal. Calcd. for $C_{17}H_{14}ClF_3O_4$: C, 54.19; H, 3.77, Cl, 9.46; F, 15.21. Found: C, 54.08; H, 4.05; Cl, 9.40; F, 15.58.

EXAMPLE 5

Preparation of N,N-Diethyl 2-[4-(2-chloro-4-trifluoromethylphenoxy phenoxy] propionamide 4-(2-Chloro-4-trifluoromethylphenoxy)phenol (5.85, 0.020 mole), N,N-diethyl 2-chloropropionamide (3.3 g, 0.020 mole), anhydrous potassium carbamate (3.2 g, >0.020 mole) and glyme are charged to a flask and heated at reflux for 18 hours. Then additional anhydrous potassium carbamate (3.0 g) and t-butyl alcohol (5 ml) are added to the reaction mixture and reflux contined for an additional 24 hours, the reaction mixture is cooled, the inorganics removed by filtration and the solvent removed from the filtrate in vacuo to give an oily residue that is dissolved in toluene (100 ml) and extracted with 2 MNaOH, washed with water, decanted and dried (anh. Na₂SO₄) to give 7.5 g of an off white solid that is recrystallized from hexane to give 5 g. of white needles, mp at 118°-19° C.

EXAMPLE 6

Preparation of 2-[4-(2-Chloro-4-trifluoromethylphenoxy)phenoxy] propionic acid Ethyl 2-[4-(2-chloro-4-trifluoromethylphenoxy)phenoxy] propionate (2.5 g, 0.0064 mole) is charged to a flask containing formic acid (25 ml) and a catalytic amount of p-toluenesulfonic acid monohydrate and the mixture heated on a steam bath for 48 hours allowing the ethyl formate to distill from the reaction mixture as it is formed.

The formic acid is then removed in vacuo to give a mushy solid that is dissolved in a 1:1 mixture of petroleum ether and toluene and extracted into 1 N sodium hydroxide. The aqueous basic layer is then decanted and acidified to pH 1 with concentrated hydrochloric acid and the product extracted into methylene chloride, dried with anhydrous sodium sulfate and the solvent removed in vacuo to give 0.89 g of product, mp 107°-8° C., after recrystallization from hexane containing a small amount of acetone.

EXAMPLE 40

Preparation of 2-[4-(4-trifluoromethylphenoxy)phenoxy] propanamide

A mixture containing 10.0 g (0.039 mole) of 4-(4-trifluoromethylphenoxy)phenol, 5.0 g (0.039 mole) of 2-chloropropanamide, 6.9 g (0.05 mole) of anhydrous potassium carbonate, and 50 ml of dimethylsulfoxide is stirred at 90° until reaction is complete, as indicated by vpc techniques. The resultant slurry is cooled, poured into 600 ml of water, and teated with 1:1 hexane/tolune, and the product is isolated by filtration, mp 147°-149°. Recrystallization from hexane affords highly pure product, mp 149-151.

EXAMPLE 41

Preparation of 2-[4-(4-trifluoromethylphenoxy)phenoxy] propionitrile

A solution containing 6.2 g (0.02 mole) of 2-[4-(4-trifluoromethylphenoxy)phenoxy] propanamide and 10.0 ml of phosphorus oxychloride in 50 ml of toluene is stirred at 50° until reaction is complete, as indictated by vpc techniques. The reaction mixture is cooled and poured into crushed ice, whereupon the toluene layer is washed with water, dried, and concentrated in vacuo. Purification is effected by elution through a pad of silica gel (50% toluene/hexane) to afford a colorless solid, mp 53°-56°.

EXAMPLE 48

Preparation of Ethyl 2-[4-(2-nitro-4-trifluoromethylphenylthio) phenoxy] propionate A mixture containing 12.6 g (0.10 mole) of 4-mercapto phenol, 7.15 g (0.05 mole) of copper (I) oxide, and 100 ml of absolute ethanol is heated at reflux under an atmosphere of dry nitrogen until conversion to the copper thiophenate is complete, as indicated by discharge of the reddish color of the copper (I) oxide. The resultant yellow mixture is cooled to 25°, 27.0 g (0.10 mole) of 4-bromo-3-nitro-benzotrifluoride, 100 ml of quinoline, and 10 ml of pyridine are added, and the reaction vessel is equipped with a Newman still head. The reaction is now slowly heated with concomitant removal of the ethanol to 90° and maintained at this temperature until the conversion is complete, as indicated by vpc techniques. The dark liquid is cooled to 70° C., cautiously poured into 500 ml of an ice cold molar hydrochloric acid solution, and filtered, whereupon the residue is extracted with several portions of ether. The combined ether extracts are washed with a 3.0 molar hydrochloric acid solution, water until neutral, a saturated sodium chloride solution, dried (magnesium sulfate), and concentrated in vacuo to afford a quantitative yield of crude product as a dark solid. Recrystalization foam ether-hexane provides yellow crystals, mp 131°-134° of 4-(2-nitro-4-trifluoromethylphenylthio)phenol. This phenol is then reacted with 2-bromopropimate by the procedure of Example 3 above to provide the desired ethyl 2-[4-(2-nitro-4-trifluoromethylphenylthio)phenoxy] propionate, m.p. 63°-64° C.

EXAMPLE 49

Preparation of Ethyl 2-[4-(2-trifluoromethylphenylsulfinyl)phenoxy]propionate To a stirred solution containing 7.4 g (0.020 mole) of ethyl 2-(4-(2-trifluoromethylphenylthio)phenoxy) propionate and a catalytic amount of sulfuric acid (3 drops) in 50 ml of glacial acetic acid is added a solution containing 2.23 g (0.021 mold) of 32% hydrogen peroxide in 10 ml of glacial acetic acid over a period of several minutes at 25°. The resultant solution is stirred for 24 hours under ambient conditions, at which time the reaction is essentially complete. After the reaction is treated with sodium bisulfite to destroy any excess peroxide the solvent is removed in vacuo at 40° and the residue taken-up in ether. The ethereal solution is washed with a 5% potassium carbonate solution until basic, water until neutral, a saturated sodium chloride solution, dried with magnesium sulfate, and concentrated in vacuo to give 6.85 g of material. The last traces of solvent are removed by exposure to high vacuum (0.1 mm) at 70° to afford ethyl 2-[4-(2-trifluoromethylphenylsulfinyl)-phenoxy] propionate.

TABLE I

Diphenyl Ethers $$CF_3-\underset{}{\text{C}_6\text{H}_3}(R^2)-O-\underset{}{\text{C}_6\text{H}_3}(R^3)-O-R^4-R^5$$

| Ex. No. | $R^2$ | $R^3$ | $R^4$ | $R^5$ | m.p.(b.p.) | | %C | %H | %Cl | %F | %N |
|---|---|---|---|---|---|---|---|---|---|---|---|
| 1 | Cl | H | —CH(CH$_3$)— | —CO$_2$C$_2$H$_5$ | 122–123(0.25mm) | Calcd | 55.60 | 4.14 | 9.11 | 14.65 | |
| | | | | | | Found | 55.79 | 4.20 | 9.48 | 14.62 | |
| 2 | Cl | H | 3-OCHCO$_2$C$_2$H$_5$<br>\|<br>CH$_3$ | | oil | Calcd | 55.61 | 4.14 | 9.11 | 14.66 | |
| | | | | | | Found | 55.27 | 4.14 | 9.40 | 1.80 | |
| 4 | Cl | H | —CH(CH$_3$)— | —CO$_2$CH$_3$ | oil | Calcd | 54.19 | 3.77 | 9.46 | 15.21 | |
| | | | | | | Found | 54.08 | 4.05 | 9.40 | 15.58 | |
| 5 | Cl | H | —CH(CH$_3$)— | —CO$_2$N(C$_2$H$_5$)$_2$ | 118–19° | Calcd | 57.77 | 5.09 | 8.53 | 13.71 | |
| | | | | | | Found | 57.85 | 5.23 | 8.74 | 13.76 | |
| 6 | Cl | H | —CH(CH$_3$)— | —COOH | 109–111° | Calcd | 53.28 | 3.35 | 9.83 | 15.80 | |
| | | | | | | Found | 53.73 | 3.44 | 9.90 | 15.51 | |
| 7 | Cl | Cl | —CH(CH$_3$)— | —CO$_2$C$_2$H$_5$ | oil | Calcd | 51.08 | 3.57 | 16.76 | 13.47 | |
| | | | | | | Found | 50.95 | 3.49 | 16.90 | 13.15 | |
| 8 | Cl | OCH$_3$ | —CH(CH$_3$)— | —CO$_2$C$_2$H$_5$ | oil | Calcd | 54.49 | 4.33 | 8.46 | NA | |
| | | | | | | Found | 54.90 | 4.47 | 8.54 | | |
| 9 | Cl | NO$_2$ | —CH(CH$_3$)— | —CO$_2$C$_2$H$_5$ | oil | Calcd | 49.84 | 3.48 | 8.17 | | 3.22 |
| | | | | | | Found | 49.77 | 3.97 | 11.21 | NA | 1.99 |
| 10 | Cl | CH$_3$ | —CH(CH$_3$)— | —CO$_2$C$_2$H$_5$ | oil | Calcd | 56.65 | 4.50 | 8.80 | | |
| | | | | | | Found | 56.78 | 4.45 | 9.09 | NA | |
| 11 | Cl | H | —CH$_2$— | —CO$_2$C$_2$H$_5$ | oil | Calcd | 54.48 | 3.76 | 9.46 | 15.20 | |
| | | | | | | Found | 55.30 | 3.56 | 9.48 | 15.04 | |
| 12 | Cl | H | —CH(CH$_3$)— | CH$_3$<br>\|<br>—COO . NH$_2$CCH$_2$C$_4$H$_9$—t<br>\|<br>CH$_3$ | 151–155° | Calcd | 58.83 | 6.38 | 7.24 | 11.03 | 2.86 |
| | | | | | | Found | 59.50 | 6.74 | 6.92 | 11.30 | 3.09 |
| 13 | Cl | H | —CH(CH$_3$)— | —COO . ½Ca | — | Calcd | 48.31 | 2.79 | 8.91 | 14.33 | |
| | | | | | | Found | 47.63 | 3.16 | 8.57 | 11.51 | |
| 14 | Cl | H | —CH(CH$_3$)— | —COO . Na | 135–142° | Calcd | 47.96 | 2.76 | 8.85 | 14.22 | |
| | | | | | | Found | 48.72 | 3.16 | 8.65 | 12.08 | |
| 15 | Cl | H | —CH(CH$_3$)— | —COO . N(C$_2$H$_4$OH)$_3$ | oil | Calcd | Not Analyzed | | | | |
| | | | | | | Found | | | | | |
| 16 | Cl | H | —CH(CH$_3$)— | —COO . NH(CH$_3$)$_2$ | — | Calcd | Not Analyzed | | | | |
| | | | | | | Found | | | | | |
| 17 | Cl | H | —CH(CH$_3$)— | —COO . NH$_3$ | — | Calcd | 50.87 | 4.00 | 9.38 | NA | 3.70 |
| | | | | | | Found | 51.05 | 4.06 | 9.39 | | 2.94 |
| 18 | Cl | H | —CH(CH$_3$)— | —CONH$_2$ | 106–110° | Calcd | 53.42 | 3.64 | 9.85 | NA | 3.89 |
| | | | | | | Found | 53.46 | 3.68 | 9.75 | | 3.78 |
| 19 | Cl | H | —CH(CH$_3$)— | —CN | oil | Calcd | 56.24 | 3.24 | 10.37 | 16.68 | |
| | | | | | | Found | 55.77 | 3.26 | 10.31 | 16.42 | |
| 20 | Cl | H | —CH(C$_2$H$_5$)— | —CO$_2$C$_2$H$_5$ | oil | Calcd | 56.65 | 4.50 | 8.80 | | |
| | | | | | | Found | 57.18 | 4.76 | 8.77 | NA | |
| 21 | Cl | H | —CH(CH$_3$)— | —CONHC$_2$H$_5$ | 92–93.5° | Calcd | 55.75 | 4.41 | 9.14 | 14.69 | 3.61 |
| | | | | | | Found | 55.67 | 4.45 | 9.37 | 14.82 | 3.90 |
| 22 | Cl | H | —CH(CH$_3$)— | —CO$_2$C$_3$H$_7$—i | oil | Calcd | 56.66 | 4.50 | 8.80 | | |
| | | | | | | Found | 56.75 | 4.46 | 8.97 | NA | |
| 23 | Cl | H | —CH(CH$_3$)— | —CO$_2$C$_4$H$_9$ | oil | Calcd | 57.63 | 4.84 | 8.51 | | |
| | | | | | | Found | 57.80 | 4.90 | 8.47 | NA | |
| 24 | Cl | H | —CH(CH$_3$)— | —CO$_2$CH$_2$CH=CH$_2$ | oil | Calcd | 56.94 | 4.02 | 8.85 | 14.22 | |
| | | | | | | Found | 57.16 | 4.07 | 8.90 | 14.55 | |
| 25 | Cl | H | —CH(CH$_3$)— | —CO$_2$CH$_2$CH$_2$OCH$_3$ | oil | Calcd | Not Analyzed | | | | |
| | | | | | | Found | | | | | |
| 26 | Cl | H | —CH(CH$_3$)— | —CO$_2$C$_8$H$_{17}$—n | oil | Calcd | 60.95 | 5.97 | 7.50 | 12.05 | |
| | | | | | | Found | 61.39 | 6.09 | 7.56 | 11.82 | |
| 27 | H | H | —CH(CH$_3$)— | —CO$_2$C$_2$H$_5$ | 165–168°(0.45mm) | Calcd | 61.02 | 4.84 | — | 16.08 | |
| | | | | | | Found | 60.98 | 4.98 | — | 15.96 | |
| 28 | Cl | H | —CH(C$_3$H$_7$—i) | —CO$_2$C$_2$H$_5$ | oil | Calcd | 57.63 | 4.84 | 8.51 | 13.67 | |
| | | | | | | Found | 57.99 | 4.88 | 8.57 | 13.38 | |
| 29 | H | H | —CH(CH$_3$)— | —COOH | 134.5–136° | Calcd | 58.90 | 4.02 | — | 17.47 | |
| | | | | | | Found | 58.95 | 4.15 | — | 13.93 | |
| 30 | Cl | H | —CH$_2$CH=CH | —CO$_2$C$_2$H$_5$ | oil | Calcd | Not Analyzed | | | | |
| | | | | | | Found | | | | | |
| 31 | Cl | H | —CH(CH$_3$)— | —CO$_2$CH$_2$CH$_2$N(CH$_3$)$_2$ | oil | Calcd | 55.63 | 4.90 | 8.21 | 13.20 | 3.24 |
| | | | | | | Found | 55.99 | 4.71 | 7.92 | 14.07 | 3.26 |
| 32 | Cl | H | —CH(CH$_3$)— | —CO$_2$C$_3$H$_7$—n | oil | Calcd | 56.65 | 4.50 | 8.80 | 14.14 | |
| | | | | | | Found | 57.15 | 4.31 | 8.49 | 14.54 | |
| 33 | Cl | H | —CH(CH$_3$)— | —CO$_2$C$_4$H$_9$—i | oil | Calcd | 57.63 | 4.84 | 8.51 | 13.62 | |
| | | | | | | Found | 57.55 | 4.75 | 8.42 | 14.20 | |
| 34 | Cl | H | —CH(CH$_3$)— | —CO$_2$C$_4$H$_9$—sec | oil | Calcd | 57.63 | 4.84 | 8.51 | 13.62 | |
| | | | | | | Found | 58.02 | 4.60 | 8.18 | 13.59 | |
| 35 | Cl | H | —CH(CH$_3$)— | —CO$_2$C$_4$H$_9$—t | oil | Calcd | 57.63 | 4.84 | 8.51 | 13.62 | |
| | | | | | | Found | 57.63 | 4.90 | 8.97 | 13.96 | |

TABLE I-continued

Diphenyl Ethers $$CF_3-\text{C}_6\text{H}_3(R^2)-O-\text{C}_6\text{H}_3(R^3)-O-R^4-R^5$$

| Ex. No. | $R^2$ | $R^3$ | $R^4$ | $R^5$ | m.p.(b.p.) | | %C | %H | %Cl | %F | %N |
|---|---|---|---|---|---|---|---|---|---|---|---|
| 36 | Cl | H | —CH(CH$_3$)— | —CO$_2$C$_6$H$_{13}$—n | oil | Calcd | 59.40 | 5.44 | 7.97 | 12.81 | |
| | | | | | | Found | 59.87 | 5.70 | 7.75 | 12.57 | |
| 37 | CN | H | —CH(CH$_3$)— | —CO$_2$C$_2$H$_5$ | oil | Calcd | 60.16 | 4.25 | — | 15.02 | 3.69 |
| | | | | | | Found | 50.06 | 4.34 | — | 14.73 | 3.92 |
| 38 | Cl | H | —CH(CH$_3$)CH$_2$CH$_2$— | —CO$_2$C$_2$H$_5$ | oil | Calcd | 57.63 | 4.84 | 8.51 | 13.67 | |
| | | | | | | Found | 55.49 | 4.15 | 9.17 | 14.66 | |
| 39 | H | H | —CH(CH$_3$)CH$_2$CH$_2$ | —CO$_2$C$_2$H$_5$ | oil | Calcd | 62.82 | 5.53 | — | 14.90 | |
| | | | | | | Found | 62.26 | 5.64 | — | 13.62 | |
| 40 | H | H | —CH(CH$_3$)— | —CONH$_2$ | 147–149° | Calcd | 59.07 | 4.33 | — | 17.52 | 4.30 |
| | | | | | | Found | 59.11 | 4.37 | — | 17.55 | 4.51 |
| 41 | H | H | —CH(CH$_3$)— | —CN | 53–56° | Calcd | 62.54 | 3.93 | — | 18.54 | 4.55 |
| | | | | | | Found | 62.67 | 3.97 | — | 18.77 | 4.83 |

TABLE II

Diphenyl Sulfides, Sulfoxides, Sulfones $$R^8, R^9\text{-C}_6\text{H}_3-X-\text{C}_6\text{H}_4-O-R^4-R^5$$

| Ex. No. | $R^8$ | $R^9$ | $R^4$ | $R^5$ | X | m.p. | | %C | %H | %Cl | %F | %S | %N |
|---|---|---|---|---|---|---|---|---|---|---|---|---|---|
| 3 | Cl | 4-CF$_3$ | —CH(CH$_3$) | —CO$_2$C$_2$H$_5$ | —S— | 64.5–65.5° | Calcd | 53.40 | 3.98 | 8.76 | 14.08 | 7.92 | |
| | | | | | | | Found | 53.05 | 3.98 | 8.95 | 14.46 | 7.95 | |
| 42 | Cl | 4-CF$_3$ | —CH(CH$_3$)— | —CO$_2$C$_2$H$_5$ | —SO— | — | Calcd | 51.37 | 3.83 | 8.42 | 13.54 | 7.62 | |
| | | | | | | | Found | 51.24 | 3.92 | 8.24 | 13.51 | 7.28 | |
| 43 | Cl | 4-CF$_3$ | —CH(CH$_3$)— | —CO$_2$C$_2$H$_5$ | —SO— | oil | Calcd | 49.49 | 3.69 | 8.12 | 13.05 | 7.34 | |
| | | | | | | | Found | 47.82 | 3.78 | 8.68 | 13.17 | 7.20 | |
| 44 | H | 2-CF$_3$ | —CH(CH$_3$)— | —CO$_2$C$_2$H$_5$ | —S— | oil | Calcd | 58.37 | 4.63 | — | 15.39 | 8.66 | |
| | | | | | | | Found | 58.21 | 4.51 | — | 14.79 | 9.04 | |
| 45 | H | 3-CF$_3$ | —CH(CH$_3$)— | —CO$_2$C$_2$H$_5$ | —S— | oil | Calcd | 8.37 | 4.63 | — | 15.39 | 8.66 | |
| | | | | | | | Found | 58.75 | 4.83 | — | 15.15 | 9.01 | |
| 46 | H | 4-CF$_3$ | —CH(CH$_3$)— | —CO$_2$C$_2$H$_5$ | —S— | oil | Calcd | 58.37 | 4.63 | — | 15.39 | 8.66 | |
| | | | | | | | Found | 58.31 | 4.70 | — | 14.92 | 8.92 | |
| 47 | CN | 4-CF$_3$ | —CH(CH$_3$)— | —CO$_2$C$_2$H$_5$ | —S— | — | Calcd | 57.71 | 4.08 | — | 14.42 | 8.11 | 3.54 |
| | | | | | | | Found | 57.39 | 3.99 | — | 14.50 | 8.48 | 3.52 |
| 48 | NO$_2$ | 4-CF$_3$ | —CH(CH$_3$)— | —CO$_2$C$_2$H$_5$ | —S— | 63–64° | Calcd | 52.04 | 3.88 | — | 13.72 | 7.72 | 3.37 |
| | | | | | | | Found | 51.83 | 3.86 | — | 13.64 | 7.97 | 3.38 |
| 49 | H | 2-CF$_3$ | —CH(CH$_3$)— | —CO$_2$C$_2$H$_5$ | —SO— | oil | Calcd | 55.95 | 4.44 | — | 14.75 | 8.30 | |
| | | | | | | | Found | 55.76 | 4.34 | — | 14.81 | 8.47 | |
| 50 | H | 3-CF$_3$ | —CH(CH$_3$)— | —CO$_2$C$_2$H$_5$ | —SO— | oil | Calcd | 55.95 | 4.44 | — | 14.75 | 8.30 | |
| | | | | | | | Found | 56.50 | 4.49 | — | 14.51 | 8.35 | |
| 51 | H | 4-CF$_3$ | —CH(CH$_3$)— | —CO$_2$C$_2$H$_5$ | —SO— | oil | Calcd | 55.95 | 4.44 | — | 14.75 | 8.30 | |
| | | | | | | | Found | 55.80 | 4.25 | — | 14.83 | 9.38 | |
| 52 | Cl | 4-CF$_3$ | —C(CH$_3$)— | —CO$_2$C$_2$H$_5$ | —S— | oil | Calcd | 54.48 | 4.33 | 8.46 | 13.61 | 7.65 | |
| | | | | | | | Found | 55.11 | 4.70 | 7.85 | 12.60 | 7.37 | |

EXAMPLE 53

This example shows the herbicidal activity of compounds of the invention. Using the procedure described below, compounds of the invention are evaluated for control of several of the following plant species:

barnyardgrass (*Echinochloa crusgalli*)
cocklebur (*Xanthium pensylvanicum*)
crabgrass (*Digitaria spp.*)
downybrome (*Bromus tectorum*)
foxtail (*Setaria spp.*)
marigold (*Tagetes spp.*)
morningglory (*Ipomoca spp.*)
yellow nutsedge (*Cyperus esculentus*)
velvetleaf (*Abutilon theophrasti*)
wild oats (*Avena fatua*)
tomato (*Lycopersicon esculentum*)
corn (*Zea mays*)
rice (*Oryza sativa*)
soybean (*Glycine max*)
wheat (*Triticum sativum*)

The following est procedure is employed. Seeds of selected crops and weeds are planted in soil in flats. For preemergence tests, the flats are treated with the test compound immediately after the planting. For postemergence tests, the seeds are allowed to germinate, and after two weeks the flats are treated with the test compound. The compound to be evaluated is dissolved in acetone, diluted with water, and sprayed over the flats using a carrier volume equivalent to 50 gallons per acre at the rate of application (pounds per acre, lb/A) specified in the tables. About two weeks after the application of the test compound, the state of growth of the plants is observed and the phytotoxic effect of the compound is evaluated. Tables III and IV give the average percent control achieved by test compounds in terms of the percent of the plants which are killed by the compounds.

TABLE III

HERBICIDAL ACTIVITY (% Control)

| Compound (Example No.) | Rate (lb./A) | Barnyard-grass | Crabgrass | Downybrome | Foxtail | Wild Oats | Tomato | Velvet-leaf | Corn | Rice | Soybean | Wheat |
|---|---|---|---|---|---|---|---|---|---|---|---|---|
| Preemergence |||||||||||||
| 1 | ½ | 99 | 100 | 0 | 100 | 0 | 0 | 0 | 0 | 0 | 0 | 0 |
| 1 | 1 | 100 | 100 | 80 | 100 | 60 | 0 | 0 | 60 | 80 | 0 | 0 |
| 1 | 2 | 100 | 100 | 90 | 100 | 99 | 0 | 0 | 99 | 100 | 0 | 0 |
| Postemergence |||||||||||||
| 1 | ½ | 100 | — | 70 | 100 | 100 | 10 | — | — | 70 | 20 | 80 |
| 1 | 1 | 100 | — | 80 | 100 | 100 | 30 | — | — | 99 | 30 | 90 |
| 1 | 2 | 100 | — | 90 | 100 | 100 | 80 | — | — | 90 | 40 | 95 |

TABLE IV

HERBICIDAL ACTIVITY (% control)

| Compound (Ex.No.) | Rate (lb/A) | Type of Application | Cocklebur | Mari-gold | Morning-glory | Tomato | Velvet-leaf | Barnyard-grass | Downy-brome | Foxtail | Nut-sedge | Wild oat |
|---|---|---|---|---|---|---|---|---|---|---|---|---|
| 1 | 2 | Pre | | | | | | | | | | |
|   | 2 | Post | | | | | | | | | | |
| 2 | 2 | Pre | 0 | 90 | 0 | 100 | 100 | 30 | 0 | 100 | 0 | 20 |
|   | 2 | Post | 90 | 90 | 100 | 100 | 100 | 60 | 40 | 50 | 0 | 50 |
| 4 | 2 | Pre | 0 | 0 | 0 | 0 | 20 | 100 | 0 | 100 | 0 | 40 |
|   | 2 | Post | 100 | 30 | 20 | 60 | 80 | 100 | 99 | 100 | 0 | 100 |
| 5 | 2 | Pre | 0 | 0 | 0 | 0 | 0 | 60 | 0 | 99 | 0 | 0 |
|   | 2 | Post | 0 | 0 | 20 | 80 | 20 | 20 | 30 | 90 | 0 | 20 |
| 6 | 2 | Pre | 0 | 0 | 0 | 0 | 0 | 100 | 40 | 100 | 0 | 20 |
|   | 2 | Post | 50 | 20 | 40 | 80 | 20 | 100 | 30 | 95 | 0 | 95 |
| 7 | 2 | Pre | 0 | 0 | 0 | 0 | 0 | 0 | 0 | 90 | 0 | 0 |
|   | 2 | Post | 80 | 20 | 100 | 80 | 80 | 10 | 0 | 40 | 0 | 20 |
| 8 | 2 | Pre | 0 | 0 | 0 | 0 | 0 | 0 | 0 | 99 | 0 | 0 |
|   | 2 | Post | 0 | 0 | 0 | 0 | 0 | 0 | 0 | 0 | 0 | 0 |
| 9 | 2 | Pre | 0 | 0 | 0 | 0 | 0 | 0 | 0 | 0 | 0 | 0 |
|   | 2 | Post | 40 | 50 | 0 | 90 | 20 | 40 | 0 | 0 | 0 | 0 |
| 10 | 2 | Pre | 0 | 0 | 0 | 0 | 0 | 0 | 0 | 0 | 0 | 0 |
|    | 2 | Post | 40 | 0 | 80 | 30 | 40 | 0 | 0 | 0 | 0 | 0 |
| 11 | 2 | Pre | 0 | 0 | 0 | 0 | 0 | 0 | 0 | 30 | 0 | 0 |
|    | 2 | Post | 50 | 0 | 30 | 0 | 20 | 20 | 0 | 30 | 0 | 40 |
| 12 | 2 | Pre | 0 | 0 | 0 | 0 | 0 | 100 | 0 | 100 | 0 | 60 |
|    | 2 | Post | 0 | 0 | 0 | 0 | 0 | 100 | 60 | 100 | 0 | 70 |
| 13 | 2 | Pre | 0 | 0 | 0 | 0 | 0 | 100 | 70 | 100 | 0 | 70 |
|    | 2 | Post | 0 | 0 | 0 | 0 | 0 | 100 | 20 | 90 | 0 | 60 |
| 14 | 2 | Pre | 0 | 0 | 0 | 0 | 0 | 100 | 50 | 100 | 0 | 40 |
|    | 2 | Post | 0 | 0 | 0 | 0 | 0 | 100 | 20 | 95 | 0 | 80 |
| 15 | 2 | Pre | 0 | 0 | 40 | 0 | 0 | 100 | 0 | 100 | 0 | 0 |
|    | 2 | Post | 0 | 0 | 0 | 0 | 0 | 90 | 0 | 90 | 0 | 20 |
| 16 | 2 | Pre | 0 | 0 | 0 | 0 | 0 | 100 | 70 | 100 | 0 | 70 |
|    | 2 | Post | 0 | 0 | 0 | 0 | 0 | 100 | 0 | 90 | 0 | 80 |
| 17 | 2 | Pre | 0 | 0 | 0 | 0 | 0 | 100 | 30 | 100 | 0 | 95 |
|    | 2 | Post | 0 | 0 | 0 | 0 | 0 | 99 | 0 | 90 | 0 | 80 |
| 18 | 2 | Pre | 0 | 0 | 0 | 0 | 0 | 100 | 95 | 100 | 0 | 0 |
|    | 2 | Post | 0 | 0 | 0 | 0 | 0 | 99 | 40 | 99 | 0 | 95 |
| 19 | 2 | Pre | 0 | 0 | 0 | 0 | 0 | 100 | 20 | 100 | 0 | 30 |
|    | 2 | Post | 0 | 0 | 0 | 0 | 0 | 99 | 30 | 99 | 0 | 90 |
| 20 | 2 | Pre | 0 | 0 | 0 | 0 | 0 | 99 | 90 | 100 | 0 | 40 |
|    | 2 | Post | 0 | 0 | 0 | 30 | 50 | 100 | 30 | 100 | 20 | 100 |
| 21 | 2 | Pre | 0 | 0 | 0 | 0 | 0 | 100 | 90 | 100 | 0 | 40 |
|    | 2 | Post | 0 | 0 | 0 | 0 | 0 | 100 | 30 | 100 | 0 | 99 |
| 22 | 2 | Pre | 0 | 0 | 0 | 0 | 0 | 100 | 95 | 100 | 0 | 60 |
|    | 2 | Post | 30 | 30 | 20 | 99 | 40 | 100 | 99 | 100 | 0 | 100 |
| 23 | 2 | Pre | 0 | 0 | 0 | 0 | 0 | 100 | 99 | 100 | 30 | 80 |
|    | 2 | Post | 0 | 30 | 20 | 99 | 40 | 100 | 99 | 100 | 0 | 100 |
| 24 | 2 | Pre | 100 | 0 | 0 | 0 | 0 | 100 | 99 | 100 | 30 | 80 |
|    | 2 | Post | 20 | 50 | 20 | 95 | 80 | 100 | 100 | 100 | 0 | 100 |
| 25 | 2 | Pre | 0 | 0 | 0 | 0 | 0 | 100 | 95 | 100 | 30 | 70 |
|    | 2 | Post | 20 | 30 | 40 | 95 | 60 | 100 | 80 | 100 | 40 | 100 |
| 26 | 2 | Pre | 0 | 0 | 0 | 0 | 0 | 50 | 0 | 0 | 0 | 50 |
|    | 2 | Post | 60 | 70 | 70 | 30 | 50 | 100 | 50 | 100 | 20 | 20 |
| 27 | 2 | Pre | 0 | 0 | 0 | 0 | 0 | 100 | 99 | 100 | 0 | 99 |
|    | 2 | Post | 70 | 100 | 95 | 60 | 40 | 100 | 100 | 100 | 0 | 100 |
| 28 | 2 | Pre | 0 | 0 | 70 | 0 | 0 | 95 | 30 | 90 | 0 | 0 |
|    | 2 | Post | 0 | 0 | 0 | 0 | 0 | 60 | 20 | 99 | 0 | 60 |

TABLE IV-continued
HERBICIDAL ACTIVITY
(% control)

| Compound (Ex.No.) | Rate (lb/A) | Type of Application | Cocklebur | Marigold | Morning-glory | Tomato | Velvet-leaf | Barnyard-grass | Downy-brome | Foxtail | Nut-sedge | Wild oat |
|---|---|---|---|---|---|---|---|---|---|---|---|---|
| 29 | 2 | Pre | 0 | 0 | 0 | 0 | 0 | 100 | 99 | 100 | 0 | 95 |
|  | 2 | Post | 0 | 30 | 0 | 30 | 0 | 100 | 80 | 100 | 0 | 100 |
| 30 | 2 | Pre | 0 | 0 | 0 | 0 | 0 | 60 | 0 | 60 | 0 | 0 |
|  | 2 | Post | 0 | 0 | 0 | 30 | 0 | 0 | 0 | 100 | 0 | 30 |
| 31 | 2 | Pre | 0 | 0 | 70 | 0 | 0 | 100 | 30 | 100 | 0 | 40 |
|  | 2 | Post | 60 | 40 | 80 | 90 | 80 | 100 | 100 | 100 | 0 | 99 |
| 32 | 2 | Pre | 0 | 0 | 0 | 0 | 0 | 100 | 80 | 100 | 0 | 80 |
|  | 2 | Post | 0 | 20 | 0 | 30 | 30 | 100 | 100 | 100 | 0 | 100 |
| 33 | 2 | Pre | 0 | 0 | 0 | 0 | 0 | 99 | 90 | 100 | 0 | 90 |
|  | 2 | Post | 0 | 0 | 0 | 0 | 0 | 100 | 100 | 100 | 0 | 100 |
| 34 | 2 | Pre | 0 | 0 | 0 | 0 | 0 | 100 | 95 | 100 | 0 | 80 |
|  | 2 | Post | 0 | 0 | 0 | 0 | 0 | 100 | 99 | 100 | 0 | 100 |
| 35 | 2 | Pre | 0 | 0 | 0 | 0 | 0 | 99 | 0 | 100 | 0 | 0 |
|  | 2 | Post | 0 | 0 | 0 | 0 | 0 | 60 | 0 | 100 | 0 | 0 |
| 36 | 2 | Pre | 0 | 0 | 0 | 0 | 0 | 100 | 0 | 100 | 0 | 0 |
|  | 2 | Post | 0 | 0 | 0 | 0 | 0 | 100 | 60 | 100 | 0 | 100 |
| 37 | 2 | Pre | 0 | 0 | 40 | 20 | 20 | 100 | 95 | 60 | 0 | 0 |
|  | 2 | Post | 30 | 10 | 10 | 30 | 0 | 100 | 90 | 95 | 0 | 90 |
| 38 | 2 | Pre | 0 | 0 | 0 | 0 | 0 | 90 | 0 | 100 | 0 | 0 |
|  | 2 | Post | 0 | 0 | 0 | 0 | 0 | 100 | 90 | 100 | 0 | 99 |
| 39 | 2 | Pre | 0 | 0 | 0 | 0 | 0 | 99 | 60 | 99 | 0 | 50 |
|  | 2 | Post | 60 | 0 | 40 | 20 | 0 | 100 | 100 | 100 | 0 | 100 |
| 40 | 2 | Pre | 0 | 0 | 0 | 0 | 0 | 99 | 80 | 100 | 0 | 60 |
|  | 2 | Post | 20 | 0 | 0 | 0 | 0 | 99 | 40 | 95 | 0 | 95 |
| 41 | 2 | Pre | 0 | 0 | 0 | 0 | 0 | 99 | 80 | 100 | 0 | 70 |
|  | 2 | Post | 0 | 0 | 0 | 0 | 0 | 100 | 40 | 60 | 0 | 99 |
| 42 | 4 | Pre | 0 | 0 | 0 | 0 | 40 | 95 | 40 | 99 | 0 | 20 |
|  | 4 | Post | 0 | 0 | 0 | 0 | 0 | 0 | 0 | 0 | 0 | 0 |
| 43 | 4 | Pre | 0 | 50 | 0 | 0 | 6 | 0 | 20 | 0 | 0 | 0 |
|  | 4 | Post | 0 | 0 | 0 | 0 | 0 | 0 | 0 | 0 | 0 | 0 |
| 44 | 8 | Pre | 0 | 0 | 0 | 0 | 30 | 80 | 60 | 0 | 0 | 0 |
|  | 4 | Post | 0 | 0 | 0 | 0 | 20 | 0 | 0 | 20 | 0 | 0 |
| 45 | 8 | Pre | 0 | 0 | 0 | 0 | 0 | 0 | 0 | 0 | 0 | 0 |
|  | 4 | Post | 0 | 0 | 0 | 80 | 0 | 20 | 20 | 30 | 0 | 20 |
| 46 | 8 | Pre | 0 | 0 | 0 | 0 | 0 | 70 | 50 | 70 | 0 | 0 |
|  | 4 | Post | 0 | 0 | 0 | 80 | 0 | 50 | 30 | 30 | 0 | 20 |
| 47 | 2 | Pre | 0 | 0 | 0 | 0 | 0 | 100 | 40 | 95 | 0 | 100 |
|  | 2 | Post | 0 | 0 | 0 | 0 | 0 | 100 | 99 | 99 | 0 | 99 |
| 48 | 2 | Pre | 0 | 0 | 0 | 0 | 0 | 95 | 30 | 95 | 0 | 0 |
|  | 2 | Post | 0 | 0 | 0 | 0 | 0 | 60 | 0 | 20 | 0 | 80 |
| 49 | 4 | Pre | 0 | 0 | 0 | 0 | 0 | 0 | 0 | 0 | 0 | 0 |
|  | 4 | Post | 0 | 0 | 0 | 20 | 20 | 20 | 0 | 20 | 0 | 30 |
| 50 | 4 | Pre | 0 | 0 | 0 | 0 | 0 | 0 | 0 | 0 | 0 | 0 |
|  | 4 | Post | 0 | 0 | 0 | 20 | 0 | 20 | 0 | 0 | 0 | 20 |
| 51 | 4 | Pre | 0 | 0 | 0 | 0 | 0 | 0 | 0 | 0 | 0 | 0 |
|  | 4 | Post | 0 | 0 | 0 | 0 | 0 | 20 | 0 | 0 | 0 | 20 |
| 52 | 4 | Pre | 0 | 0 | 0 | 0 | 0 | 40 | 0 | 70 | 0 | 0 |
|  | 4 | Post | 0 | 0 | 0 | 0 | 0 | 0 | 0 | 0 | 0 | 0 |
| 3 | 2 | Pre | 0 | 0 | 0 | 0 | 0 | 95 | 40 | 100 | 0 | 30 |
|  | 2 | Post | 20 | 50 | 50 | 70 | 70 | 70 | 90 | 100 | 66 | 99 |

It should be understood that changes and variations may be made without departing from the spirit and scope of the invention as defined by the appended claims.

We claim:
1. A compound of the formula

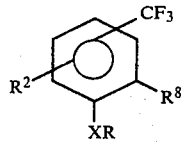

wherein
R[8] is a hydrogen atom, a halogen atom, a cyano group, a ($C_1$-$C_4$) alkyl group, a ($C_1$-$C_4$) alkoxy group, or a trifluoromethyl group,
R[2] is a hydrogen atom, a halogen atom or a cyano group
R is a group of the formula

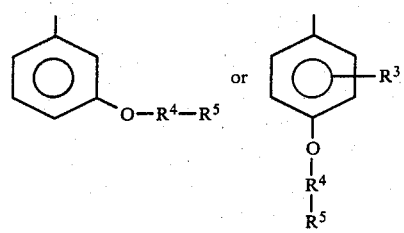

wherein
R[3] is a hydrogen atom, a halogen atom, a ($C_1$-$C_4$) alkyl group, or a ($C_1$-$C_4$) alkoxy group,
R[4] is a divalent ($C_1$-$C_5$) alkylene group,
R[5] is a cyano group or a group of the formula —COR[6], wherein R[6] is a ($C_1$-$C_{10}$) alkoxy group, a hydroxy group or an agronomically-acceptable salt thereof, a ($C_1$-$C_4$) alkoxy ($C_1$-$C_4$) alkoxy group, an amino group, a ($C_1$-$C_4$) alkylamino group, a di(C-

$_1$–C$_4$) alkylamino group, an amino (C$_1$–C$_4$) alkoxy group, a (C$_1$–C$_4$) alkylamino (C$_1$–C$_4$) alkoxy group, or a di(C$_1$–C$_4$) alkylamino (C$_1$–C$_4$) alkoxy group, and X is a sulfur atom, a sulfinyl group, or a sulfonyl group.

2. The compound of claim 1 wherein R is a group of the formula

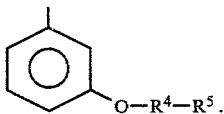

3. The compound of claim 1 wherein R is a group of the formula

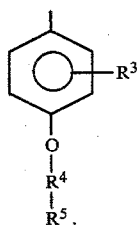

4. The compound of claim 3 wherein R$^3$ is a hydrogen atom.

5. The compound of claim 4 wherein R$^2$ is a hydrogen atom.

6. The compound of claim 5 wherein R$^4$ is a group of the formula —CHR$^7$— wherein R$^7$ is a hydrogen atom or a (C$_1$–C$_4$) alkyl group.

7. The compound of claim 6 wherein R$^5$ is a cyano group.

8. The compound of claim 6 wherein R$^5$ is a group of the formula —COR$^6$.

9. The compound of claim 8 wherein R$^7$ is a methyl group.

10. The compound of claim 9 wherein R$^6$ is a (C$_1$–C$_6$) alkoxy group.

11. The compound of claim 1 wherein X is a sulfur atom.

12. The compound of claim 1 wherein X is a sulfinyl group.

13. The compound of claim 1 wherein X is a sulfonyl group.

14. The compound of claim 9 wherein R$^6$ is a hydroxy group or an agronomically-acceptable salt thereof.

15. A herbicidal composition comprising a compound of claim 1 and an agronomically-acceptable carrier.

16. A method for controlling weeds which comprises applying to the growth medium prior to the emergence of the weeds from the growth medium a compound of claim 1 in an amount sufficient to control the growth of the weeds.

17. The method of claim 16 wherein the weeds are monocots.

18. A method for controlling weeds which comprises applying to weed seedlings a compound of claim 1 in an amount sufficient to control the growth of the seedlings.

19. The method of claim 18 wherein the weeds are monocots.

* * * * *